(12) United States Patent
Lento

(10) Patent No.: US 11,826,211 B2
(45) Date of Patent: Nov. 28, 2023

(54) INSTRUMENT PRODUCT AND A METHOD FOR MANUFACTURING THE SAME

(71) Applicant: LM-INSTRUMENTS OY, Parainen (FI)

(72) Inventor: Jaakko Lento, Parainen (FI)

(73) Assignee: LM-Instruments OY, Parainen (FI)

( * ) Notice: Subject to any disclaimer, the term of this patent is extended or adjusted under 35 U.S.C. 154(b) by 924 days.

(21) Appl. No.: 16/494,354

(22) PCT Filed: Mar. 16, 2018

(86) PCT No.: PCT/FI2018/050196
§ 371 (c)(1),
(2) Date: Sep. 16, 2019

(87) PCT Pub. No.: WO2018/167373
PCT Pub. Date: Sep. 20, 2018

(65) Prior Publication Data
US 2020/0129267 A1    Apr. 30, 2020

(30) Foreign Application Priority Data
Mar. 16, 2017  (FI) ..................................... 20175234

(51) Int. Cl.
*H01Q 1/22* (2006.01)
*A61B 90/98* (2016.01)
(Continued)

(52) U.S. Cl.
CPC ................ *A61B 90/98* (2016.02); *A61C 3/00* (2013.01); *G06K 19/0776* (2013.01); *G06K 19/07758* (2013.01); *A61C 2204/005* (2013.01)

(58) Field of Classification Search
CPC . A61B 2090/0813; A61B 90/98; A61B 90/90; A61B 2017/00526;
(Continued)

(56) References Cited

U.S. PATENT DOCUMENTS

2016/0128798 A1    5/2016  Bovet et al.
2016/0296299 A1*  10/2016  Mortensen ............. A61B 90/90
(Continued)

FOREIGN PATENT DOCUMENTS

WO    2007066204 A2    6/2007
WO    2008062387 A3    5/2008
(Continued)

OTHER PUBLICATIONS

International Search Report for PCT Application No. PCT/FI2018/050196, dated Jun. 7, 2018, 4 pages.

*Primary Examiner* — Dionne Pendleton
(74) *Attorney, Agent, or Firm* — Lippes Mathias LLP

(57) ABSTRACT

An instrument product comprises a medical hand instrument (101) and a radio frequency identifier (102) readable from a distance away from the radio frequency identifier. The radio frequency identifier is at least partly covered with cover material (103) attached with adhesive material to a surface of the medical hand instrument so that the adhesive material is in contact with both the cover materia! and the surface of the medical hand instrument. The cover material can be the same material as the adhesive material, or the cover material may constitute a cover element which comprises a cavity for the radio frequency identifier and which is attached with the adhesive material to the surface of the medical hand instrument.

20 Claims, 6 Drawing Sheets

(51) Int. Cl.
*A61C 3/00* (2006.01)
*G06K 19/077* (2006.01)

(58) Field of Classification Search
CPC .... A61B 2017/00951; A61B 2050/002; A61B 2090/0805; A61B 2017/00221; A61B 2017/00442; A61B 2018/00988; A61B 2050/005; A61B 2050/0056; A61B 2090/0818; A61B 42/10; A61B 46/00; A61B 50/13; A61B 50/30; A61B 50/33; A61C 2204/005; A61C 3/00; G06K 19/07758; G06K 19/0776; G06K 19/0723; G06K 19/07749; G06K 19/02; G06K 19/027; G06K 19/0726; G06K 19/07718; G06K 19/07754; G06K 19/07756; G06K 19/07771; G06K 19/07773; G06K 19/07786; G06K 7/10356; G06K 7/10396; B29L 2007/004; B29C 65/02; B29C 65/48; B29C 65/70; A61F 13/36; A61F 13/44; A61F 15/00; A61F 2013/15878; G08B 21/0275; G08B 21/24; G16H 20/40; G16H 40/20; G16H 40/63; H01Q 1/2216; Y10T 156/1082
See application file for complete search history.

(56) References Cited

U.S. PATENT DOCUMENTS

| | | | |
|---|---|---|---|
| 2017/0258551 A1* | 9/2017 | Smith | G16H 40/20 |
| 2018/0098822 A1* | 4/2018 | Bilsøe | A61B 90/98 |
| 2018/0256286 A1* | 9/2018 | Liu | G06K 19/0723 |

FOREIGN PATENT DOCUMENTS

| | | |
|---|---|---|
| WO | 2011054355 A2 | 5/2011 |
| WO | 2011075433 A1 | 6/2011 |
| WO | 2016166284 A1 | 10/2016 |

* cited by examiner

INSTRUMENT PRODUCT AND A METHOD FOR MANUFACTURING THE SAME

FIELD OF THE DISCLOSURE

The disclosure relates to an instrument product and to a method for manufacturing the same. The instrument product comprises a medical hand instrument that can be, for example but not necessarily, a dental or surgical instrument.

BACKGROUND

In many cases, authorities and actors of the medical and/or dental field want to have an infallible and traceable solution to follow instruments so as be able to trace disinfection, sterilization, reparation, and other operations directed to or carried out with the instruments under consideration. Nowadays, users do not typically have the time and willingness to generate reports manually because of the related workload. In addition, there is a risk of errors with manual data recording and identification of instruments, which prevents regarding the manually recorded data as an irrefutable proof of what has been done and what has been not done.

WO2008062387 describes an instrument comprising a radio frequency identifier "RFID". The radio frequency identifier is embedded in a polymer sheet that is attached on a surface of the handle of the instrument. The polymer sheet that includes the radio frequency identifier can be, for example, wrapped around the handle of the instrument. In order to obtain an even surface, it is possible to provide the instrument with a recess corresponding in size to the polymer sheet. In an advantageous embodiment described in WO2008062387, the polymer sheet comprises two layers between which the radio frequency identifier is located. The two layers are made of materials having different hardness. The layer of the harder material is against the instrument in order to obtain a better adhesion. The softer material protects the radio frequency identifier against external mechanical impacts. It may be, however, in some circumstances hard to guarantee that the polymer sheet remains firmly attached to the handle of the instrument. Furthermore, in some cases the shape of the handle may deviate from a cylindrical shape so that slits are left between the polymer sheet and the handle when the polymer sheet is wrapped around the handle. The slits are undesirable because, in some circumstances, they may collect impurities. For example, the shape of handles of pliers deviates typically significantly from a cylindrical shape.

SUMMARY

The following presents a simplified summary in order to provide a basic understanding of some aspects of various embodiments of the invention. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new instrument product that comprises:
  a medical hand instrument, and
  a radio frequency identifier "RFID" on a surface of the medical hand instrument, the radio frequency identifier being readable from a distance away from the radio frequency identifier.

In one preferable embodiment,
  the radio frequency identifier has an elongated shape and an end-portion of the radio frequency identifier is capable of emitting stronger radiation than another end-portion of the radio frequency identifier,
  the surface of the medical hand instrument is a surface of an elongated element of the medical hand instrument, and
  the radio frequency identifier is located at an end-portion of the elongated element of the medical hand instrument so that i) longitudinal directions of the elongated element of the medical hand instrument and the radio frequency identifier are substantially parallel with each other and ii) the end-portion (210) of the radio frequency identifier capable of emitting stronger radiation points towards a middle area of the medical hand instrument.

The radio frequency identifier is at least partly covered with cover material attached with adhesive material to the surface of the medical hand instrument so that the adhesive material is in contact with both the cover material and the surface of the medical hand instrument. The cover material can be the same material as the adhesive material and it can be arranged, e.g. cast or dispensed, to cover the radio frequency identifier after the radio frequency identifier has been attached to the surface of the medical hand instrument or simultaneously when the radio frequency identifier is being attached to the surface of the medical hand instrument. Alternatively, the cover material may constitute a cover element which comprises a cavity for the radio frequency identifier and which is attached with the adhesive material to the surface of the medical hand instrument. The adhesive material is dispensable in fluidic form prior to its curing, and thus the adhesive material can adapt with different shapes of the surface of the medical hand instrument. Therefore, slits which may collect impurities in some circumstances can be avoided. The adhesive material can be for example suitable silicone based adhesive or suitable epoxy resin based adhesive.

The above-mentioned medical hand instrument can be, for example but not necessarily, a dental or surgical hand instrument.

In accordance with the invention, there is provided also a new method for manufacturing an instrument product that comprises a medical hand instrument and a radio frequency identifier readable from a distance away from the radio frequency identifier.

The method comprises placing the radio frequency identifier on a surface of the medical hand instrument and covering the radio frequency identifier at least partly with cover material so that the cover material gets attached with adhesive material to the surface of the medical hand instrument so that the adhesive material is in contact with both the cover material and the surface of the medical hand instrument, wherein the adhesive material is dispensed in fluidic form and allowed to cure.

In one preferable embodiment of the above-mentioned method:
  the radio frequency identifier has an elongated shape and an end-portion of the radio frequency identifier is capable of emitting stronger radiation than another end-portion of the radio frequency identifier,
  the surface of the medical hand instrument is a surface of an elongated element of the medical hand instrument, and
  the radio frequency identifier is placed on an end-portion of the elongated element of the medical hand instrument so that i) longitudinal directions of the elongated element of the medical hand instrument and the radio frequency identifier are substantially parallel with each other and ii) the end-portion of the radio frequency identifier capable of emitting stronger radiation points towards a middle area of the medical hand instrument.

A number of exemplifying and non-limiting embodiments of the invention are described in accompanied dependent claims.

Various exemplifying and non-limiting embodiments of the invention both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of un-recited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF THE FIGURES

Exemplifying and non-limiting embodiments of the invention and their advantages are explained in greater detail below in the sense of examples and with reference to the accompanying drawings, in which.

DESCRIPTION OF EXEMPLIFYING AND NON-LIMITING EMBODIMENTS

The specific examples provided in the description below should not be construed as limiting the scope and/or the applicability of the accompanied claims. Lists and groups of examples provided in the description are not exhaustive unless otherwise explicitly stated.

Figure 1A:
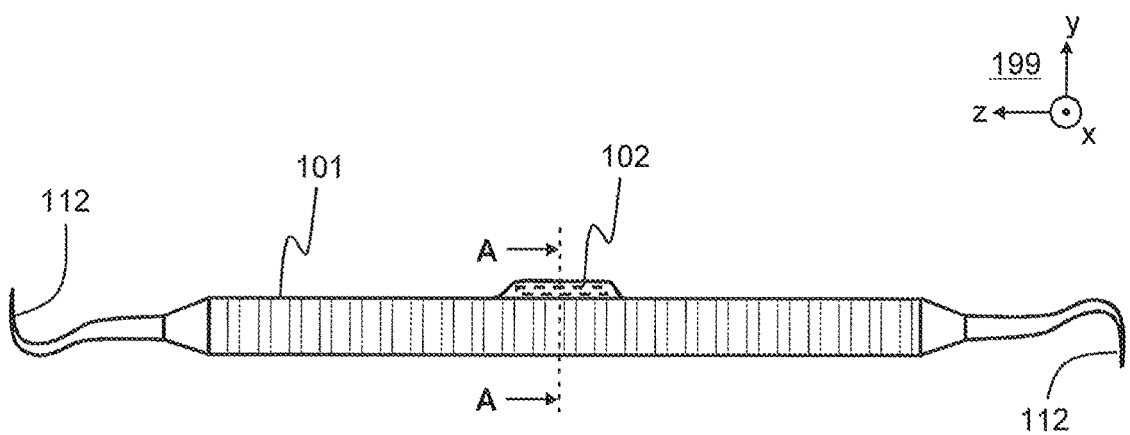
FIGS. 1a and 1b illustrate an instrument product according to an exemplifying and non-limiting embodiment of the invention.
Figure 1A:
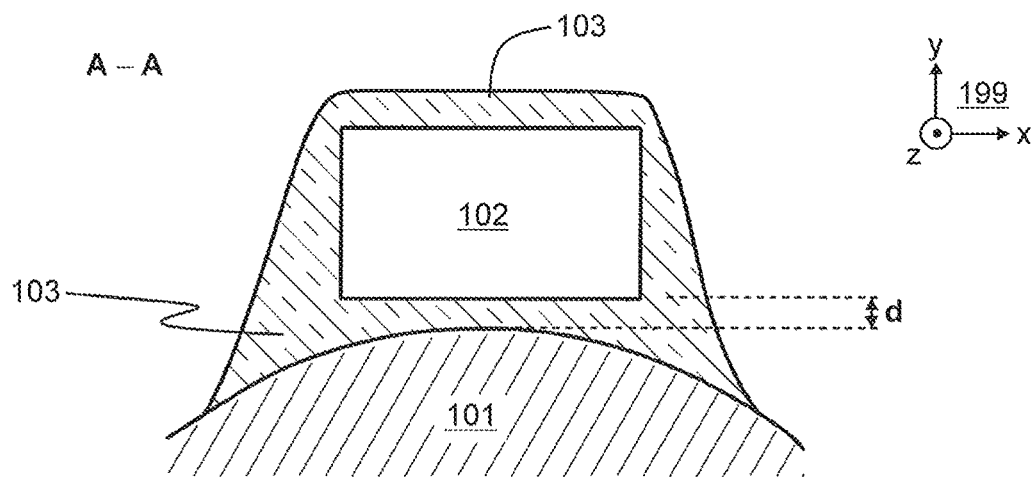
Figure 1B:
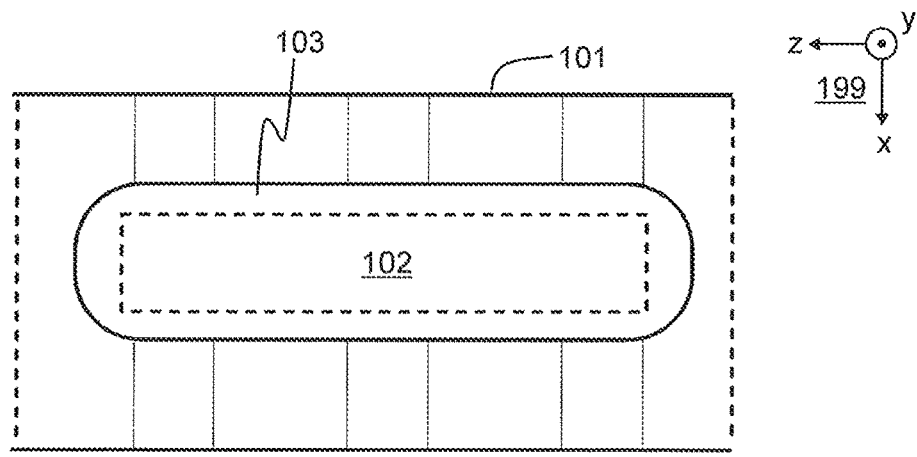

FIG. 1a shows a side-view of an instrument product according to an exemplifying and non-limiting embodiment of the invention. FIG. 1a shows also a part of a section taken along a line A-A so that the section plane is parallel with the xy-plane of a coordinate system 199. FIG. 1b shows a part of the instrument product when seen along the negative y-direction of the coordinate system 199. The instrument product comprises a medical hand instrument 101 and a radio frequency identifier "RFID" 102 that can be, for example but not necessarily, a ceramic radio frequency identifier tag. In FIG. 1b and in the side-view shown in FIG. 1a, the radio frequency identifier 102 is depicted with dashed lines. The radio frequency identifier 102 is readable from a distance away from the radio frequency identifier. The radio frequency identifier 102 may comprise, for example but not necessarily, a memory circuit capable of storing digital information. The digital information may contain for example identifying information identifying the medical hand instrument 101 as an individual object from among similar medical hand instruments and/or information indicating e.g. the date of manufacture of the medical hand instrument, the manufacturer of the medical hand instrument and/or other information related directly or indirectly to the medical hand instrument. Furthermore, the digital information may indicate the number of maintenance and/or sterilization cycles. It is however also possible that the radio frequency identifier 102 does not comprise any memory circuit but identification information related to the radio frequency identifier 102 is represented by e.g. radiation properties of the radio frequency identifier 102. In the exemplifying case illustrated in FIGS. 1a and 1b, the medical hand instrument 101 is a dental instrument suitable for e.g. removing dental calculus. The medical hand instrument comprises operative portions 112 for performing the operations according to the purpose of use of the medical hand instrument. The medical hand instrument 101 further comprises a handle that is mechanically connected to the operative portions 112 as illustrated in FIG. 1a.

In the exemplifying instrument product illustrated in FIGS. 1a and 1b, the radio frequency identifier 102 is covered with adhesive material 103 that attaches to a surface of the medical hand instrument 101. The adhesive material 103 is such that it is dispensable in fluidic form prior to its curing. The adhesive material 103 can be for example suitable silicone based adhesive. In many cases, the surface of the medical hand instrument 101 is advantageously pretreated with suitable primer, e.g. silane, in order to provide a better attachment between the adhesive material 103 and the medical hand instrument 101. The above-mentioned surface of the medical hand instrument 101 can be a metal surface or a surface of some other material such as e.g. plastic. As the adhesive material 103 is fluidic prior to its curing, the adhesive material 103 can adapt with different shapes of the surface of the medical hand instrument 101 and thereby slits which may collect impurities in some circumstances can be avoided. In the exemplifying medical hand instrument 101, the handle comprises circumferential grooves so as to provide a better grip. The adhesive material 103 which is fluidic prior to its curing can adapt with the circumferential grooves of the handle.

In the exemplifying instrument product illustrated in FIGS. 1a and 1b, the radio frequency identifier 102 is fully covered with the adhesive material 103. It is, however, also possible that e.g. the upper surface of the radio frequency identifier is not covered by the adhesive material 103. In an instrument product according an exemplifying and non-limiting embodiment of the invention, at least 90% of the surface area the radio frequency identifier is covered by the adhesive material. In an instrument product according an exemplifying and non-limiting embodiment of the invention, at least 95% of the surface area the radio frequency identifier is covered by the adhesive material.

In cases where the handle of the medical hand instrument 101 is made of metal or comprises metal, the medical hand instrument 101 can act as an external antenna for the radio frequency identifier 102. In order to achieve proper antenna operation, the radio frequency identifier 102 is advantageously positioned so that the distance d between the surface of the medical hand instrument 101 and the radio frequency identifier 102 is less than 1 mm, more advantageously less than 0.5 mm, yet more advantageously less than 0.2 mm, and yet more advantageously less than 0.05 mm. The radio frequency used by the radio frequency identifier 102 is advantageously selected so that the wavelength of the radio waves is compatible with the physical length of the medical hand instrument 101. The wave length of the radio waves can be about e.g. 300 mm.

Figure 2A:
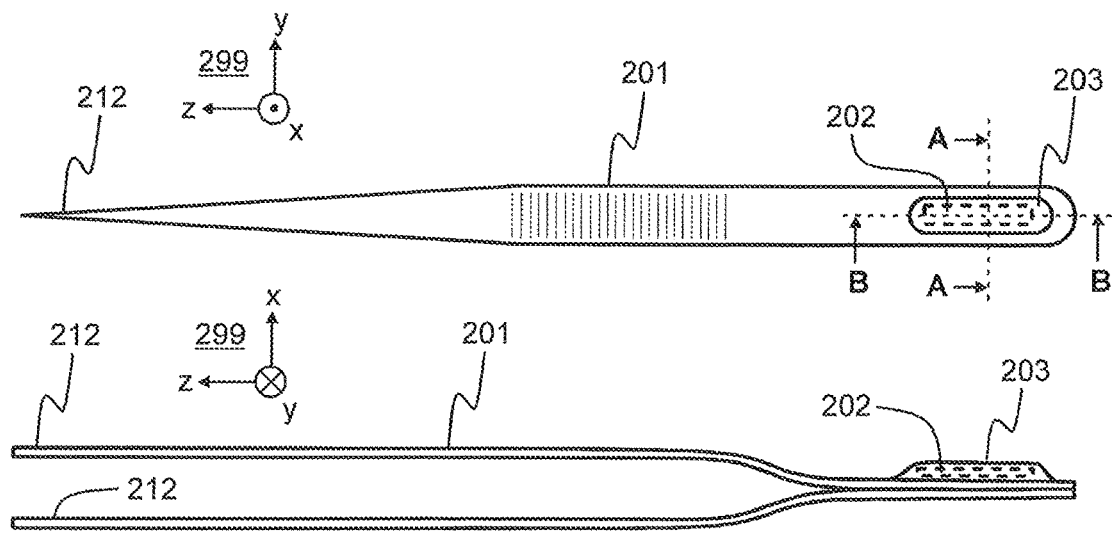
FIGS. 2a, 2b, and 2c illustrate an instrument product according to another exemplifying and non-limiting embodiment of the invention.
Figure 2B:
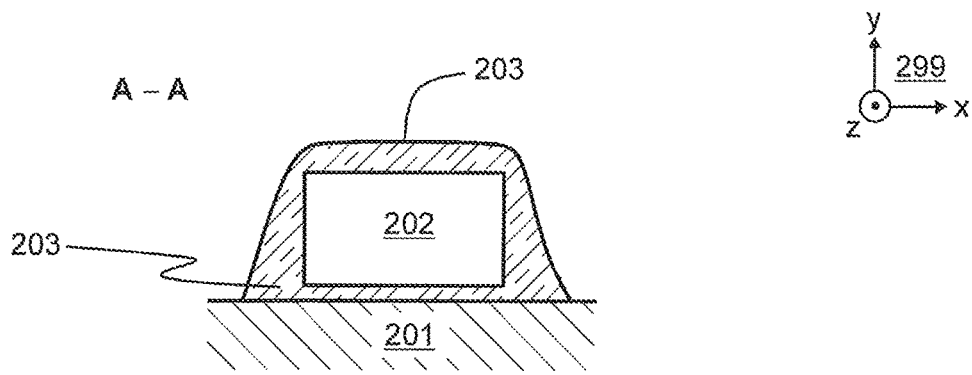
Figure 2C:
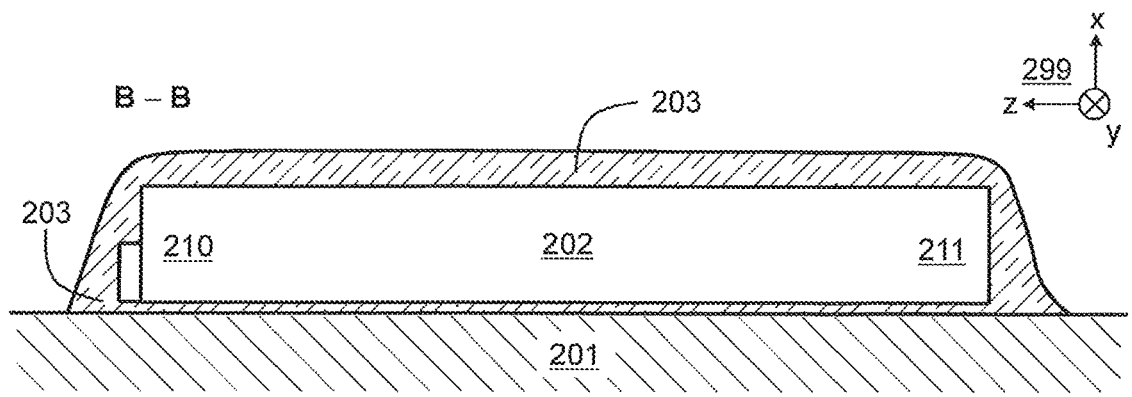

FIG. 2a shows side-views of an instrument product according to an exemplifying and non-limiting embodiment of the invention. FIG. 2b shows a part of a section taken along a line A-A shown in FIG. 2a. FIG. 2c shows a part of a section taken along a line B-B shown in FIG. 2a. The section plane related to FIG. 2b is parallel with the xy-plane of a coordinate system 299, and the section plane related to FIG. 2c is parallel with the xz-plane of the coordinate system 299. The instrument product comprises a medical hand instrument 201 and a radio frequency identifier "RFID" 202. In FIG. 2a, the radio frequency identifier 202 is depicted with dashed lines. The radio frequency identifier "RFID" 102 is readable from a distance away from the radio frequency identifier. The radio frequency identifier 202 is covered with adhesive material 203 that attaches to a surface of the medical hand instrument 201. In the exemplifying case illustrated in FIGS. 2a-2c, the medical hand instrument 201 is tweezers.

In the exemplifying instrument products illustrated in FIGS. 1a and 1b and in FIGS. 2a-2c, the radio frequency identifier is located on a surface of an elongated element of the medical hand instrument. In the instrument product illustrated in FIGS. 1a and 1b, the elongated element is the handle of the medical hand instrument 101. In the instrument product illustrated in FIGS. 2a-2c, the elongated element is a metal strip constituting one half of the tweezers. Concerning the operation of the radio frequency identifier, the radio frequency identifier is located advantageously in the middle area of the above-mentioned elongated element as is the case in the instrument product illustrated in FIGS. 1a and 1b. In the instrument product illustrated in FIGS. 2a-2c, the radio frequency identifier 202 is placed on the head of the tweezers because the radio frequency identifier might disturb a user of the tweezers if the radio frequency identifier 202 were placed in the middle of the metal strip constituting the one half of the tweezers.

In the exemplifying instrument products illustrated in FIGS. 1a and 1b and in FIGS. 2a-2c, the radio frequency identifier has an elongated shape and the longitudinal direction of the radio frequency identifier is substantially parallel with the longitudinal direction of the above-mentioned elongated element of the medical hand instrument. In the exemplifying instrument product illustrated in FIGS. 2a-2c, the radio frequency identifier 202 is positioned so that an end-portion 210 of the radio frequency identifier 202 that is capable of emitting stronger radiation than the other end-portion 211 of the radio frequency identifier 202 points towards the middle area of the medical hand instrument 201. This arrangement improves the operation of the radio frequency identifier 202 in this instrument product where the radio frequency identifier 202 is on the head of the tweezers, i.e. not in the middle area of the metal strip constituting the one half of the tweezers.

Figure 3A:
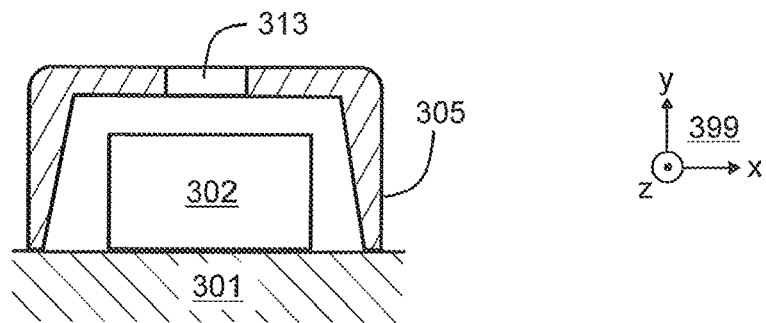
FIGS. 3a, 3b, and 3c illustrate a manufacturing process of a detail of an instrument product according to an exemplifying and non-limiting embodiment of the invention.
Figure 3B:
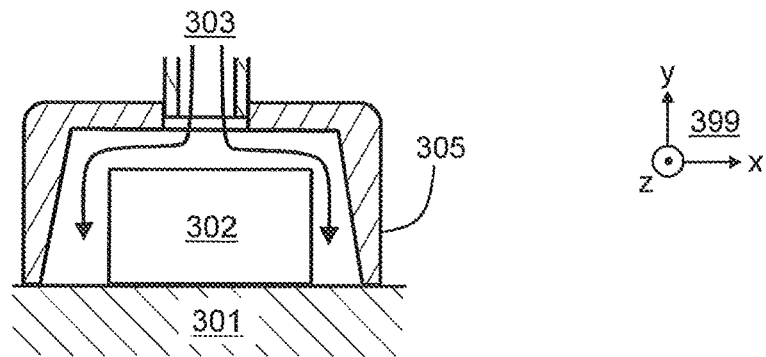
Figure 3C:
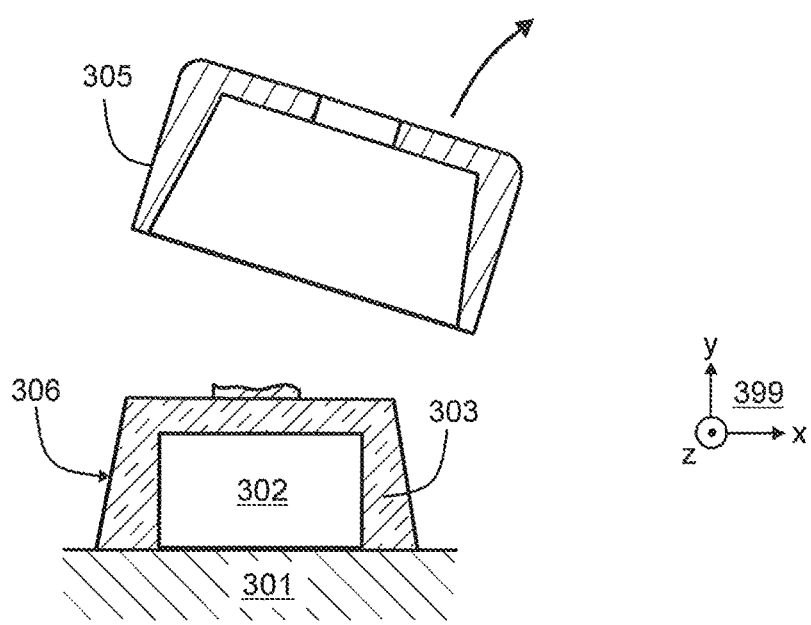
Figure 3D:
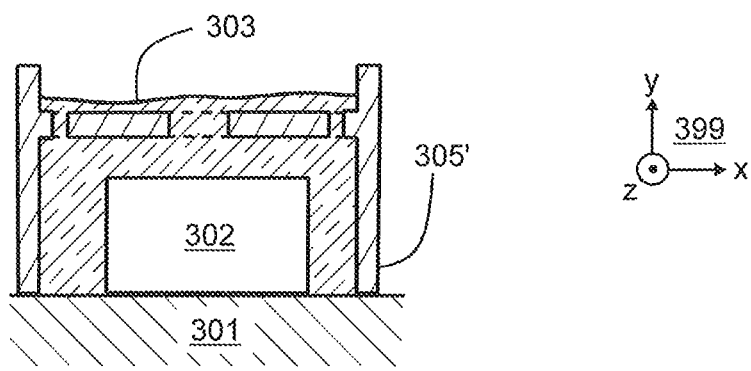
FIG. 3d illustrates a detail of an instrument product according to an exemplifying and non-limiting embodiment of the invention

FIGS. 3a, 3b, and 3c illustrate a manufacturing process of a detail of an instrument product according to an exemplifying and non-limiting embodiment of the invention. Each of FIGS. 3a-3c shows a section view where the section plane is parallel with the xy-plane of a coordinate system 399. The instrument product comprises a medical hand instrument 301 a part of which is shown in FIGS. 3a-3c. Furthermore, the instrument product comprises a radio frequency identifier 302. In this exemplifying case, a mold element 305 is used in the manufacture of the instrument product. FIG. 3a illustrates a situation where the radio frequency identifier 302 has been placed on a surface of the medical hand instrument 301 and the mold element 315 has been placed to surround the radio frequency identifier 302. FIG. 3b illustrates a situation where adhesive material 303 is injected via an aperture 313 of the mold element 305 into free spaces in the mold element 305. FIG. 3c illustrates a situation where the adhesive material 303 has cured, i.e. solidified, and the mold element 305 has been removed. In this exemplifying case, the shape of a surface 306 of the solidified adhesive material 303 is determined by the mold element 305. As the mold element 305 is removed, the surface 306 of the solidified adhesive material constitutes a part of the outer surface of the instrument product. It is also possible that the mold element 305 is not removed and thereby the mold element 305 is an element of the instrument product. FIG. 3d show a section view of a detail of an instrument product where the mold element 305' is an element of the instrument product. As illustrated in FIG. 3d, the mold element 305' is designed so that the adhesive material 303 binds the mold element 305' to be an element of the instrument product.

Figure 4A:
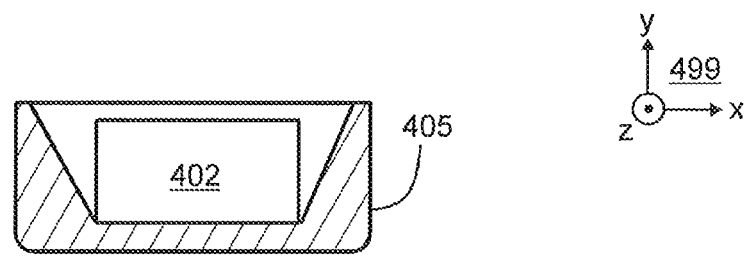
FIGS. 4a, 4b, and 4c illustrate a manufacturing process of a detail of an instrument product according to an exemplifying and non-limiting embodiment of the invention.
Figure 4B:
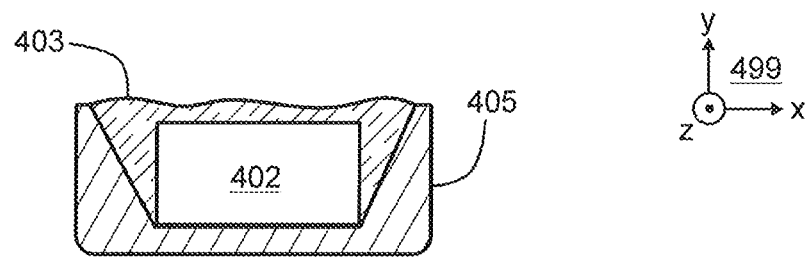
Figure 4C:
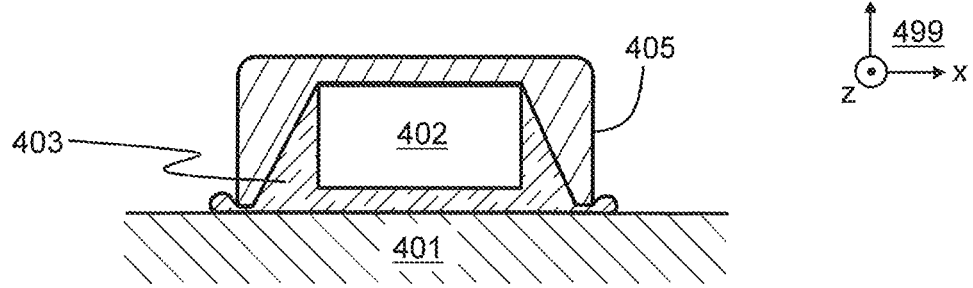

FIGS. 4a, 4b, and 4c illustrate a manufacturing process of a detail of an instrument product according to an exemplifying and non-limiting embodiment of the invention. Each of FIGS. 4a-4c shows a section view where the section plane is parallel with the xy-plane of a coordinate system 499. The instrument product comprises a medical hand instrument 401 a part of which is shown in FIG. 4c. Furthermore, the instrument product comprises a radio frequency identifier 402. In this exemplifying case, a mold element 405 is used in the manufacture of the instrument product. FIG. 4a illustrates a situation where the radio frequency identifier 402 has been placed on the bottom of the mold element 405. FIG. 4b illustrates a situation where free spaces in the mold element 405 have been filled with adhesive material 403. FIG. 4c illustrates a situation where the mold element 405 containing the adhesive material 403 and the radio frequency identifier 402 has been pressed against the surface of the medical hand instrument 401. As shown in FIG. 4c, a part of the adhesive material 403 is extruded out from the mold element 405.

Figure 5A:
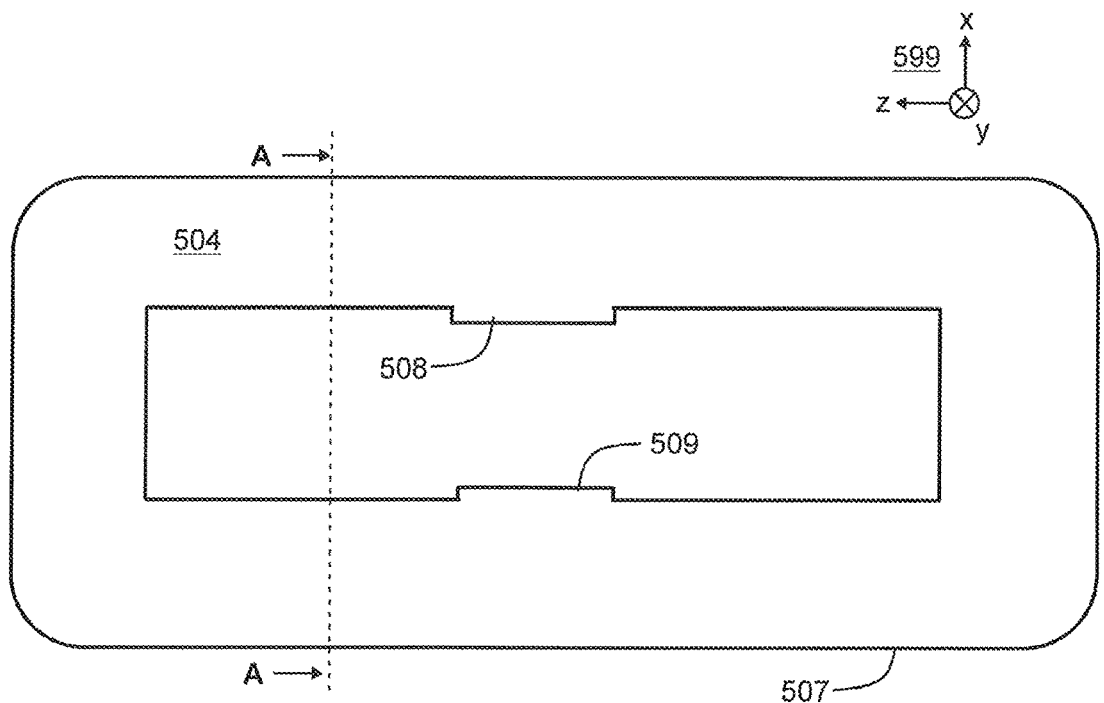
FIGS. 5a, 5b, and 5c illustrate a detail of an instrument product according to an exemplifying and non-limiting embodiment of the invention.
Figure 5B:
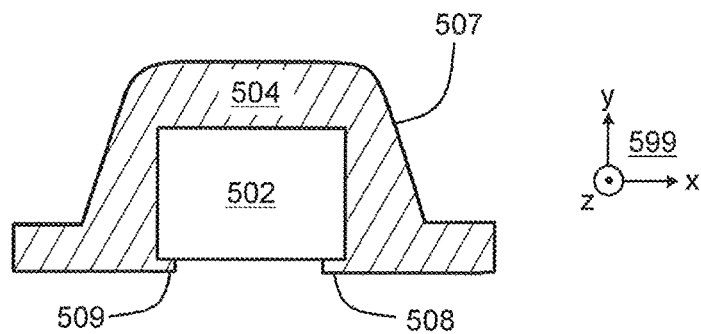
Figure 5C:
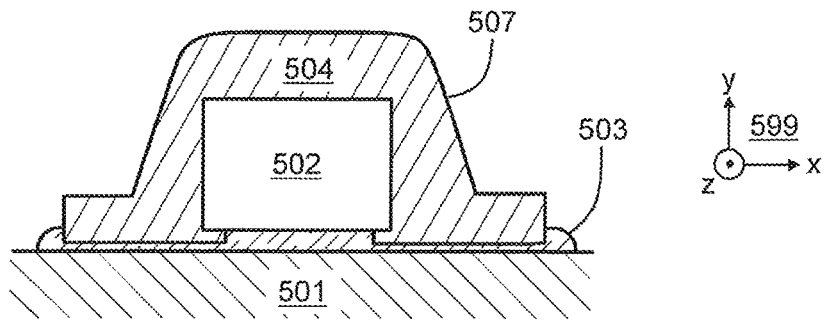

FIGS. 5a, 5b, and 5c illustrate a detail of an instrument product according to an exemplifying and non-limiting embodiment of the invention. The instrument product comprises a medical hand instrument 501 a part of which is shown in FIG. 5c. The instrument product comprises a radio frequency identifier 502. In this exemplifying case, the instrument product further comprises a cover element 507 made of suitable cover material 504. Each of FIGS. 5b and 5c shows a section view where the section plane is parallel with the xy-plane of a coordinate system 599. FIG. 5a shows a bottom view of the cover element 507. The cover element 507 comprises a cavity for the radio frequency identifier 502. As illustrated in FIG. 5c, the cover element 507 is attached with adhesive material 503 to the surface of the medical hand instrument 501 so that the cavity opens towards the surface of the medical hand instrument 501. The cover element 507 is advantageously made of flexible material and the cavity is advantageously dimensioned so that the cover element 507 gets stretched in response to insertion of the radio frequency identifier 502 in the cavity. Thus, the radio frequency identifier 502 is held in the cavity by friction force. This facilitates the process for attaching the combination of the cover element 507 and the radio frequency identifier 502 to the surface of the medical hand instrument 501. It is also possible that the edge portion of the cavity is provided with one or more claw sections 508 and 509 for shape-locking the radio frequency identifier 502 inside the cavity of the cover element 507.

In instrument products according to exemplifying and non-limiting embodiments of the invention, the cover material that at least partly covers the radio frequency identifier is advantageously flexible and soft enough to protect the radio frequency identifier against external mechanical impacts. It is advantageous that the cover material and also the adhesive material after curing are flexible because different materials of the instrument product may have different coefficients of thermal expansion and the flexibility reduces mechanical stresses caused by differences in thermal expansions.

The materials of instrument products according to exemplifying and non-limiting embodiments of the invention are advantageously selected so that the instrument products are suitable for autoclave sterilization with sufficient temperature and duration and for a sufficient number of sterilization cycles. The sterilization temperature can be e.g. 134° C. or 121° C., and the duration of each sterilization cycle can be e.g. 3-6 minutes or sometimes more. An instrument product is advantageously capable of withstanding at least 1000 sterilization cycles of the kind mentioned above.

Figure 6:
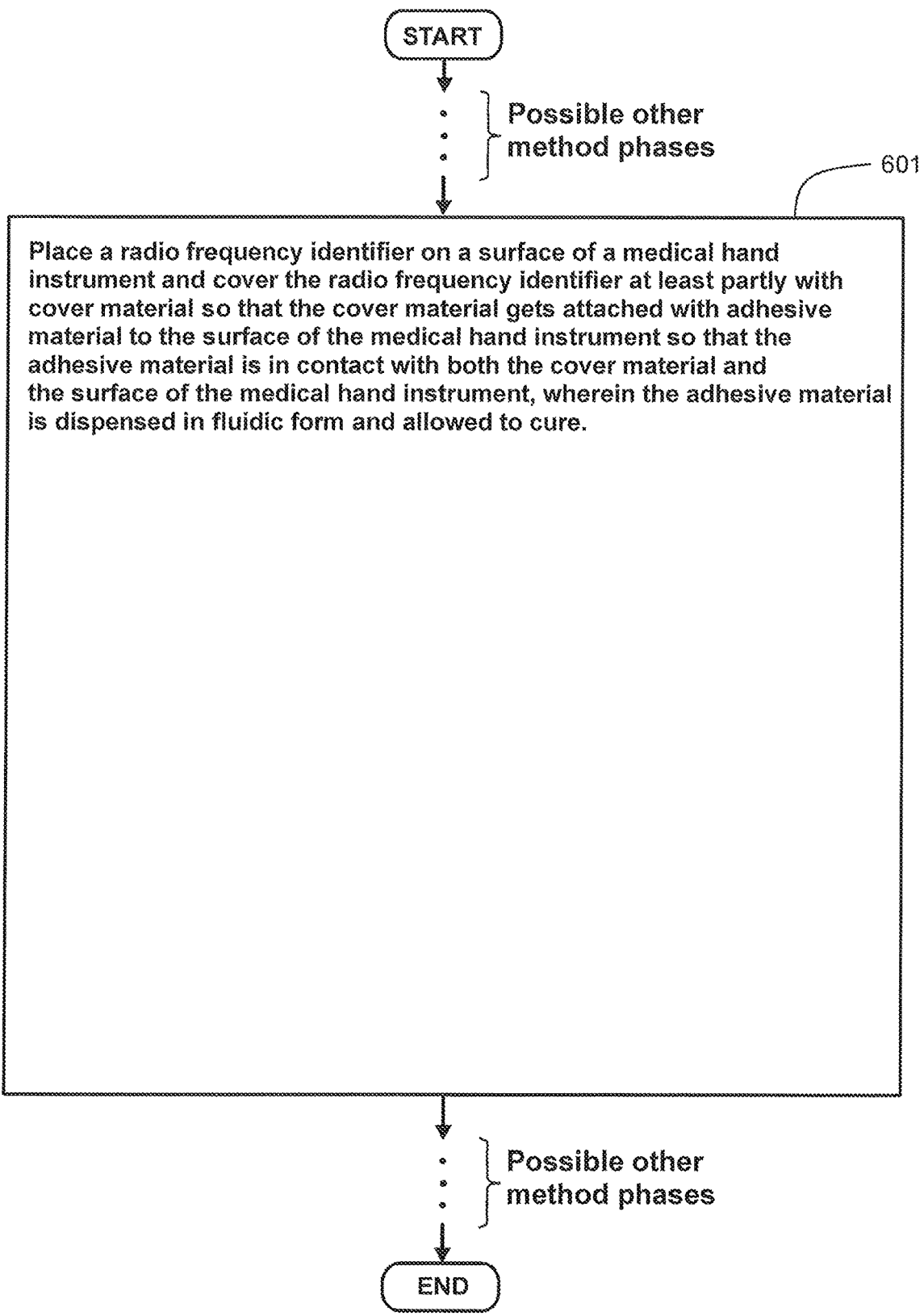
FIG. 6 shows a flowchart of a method according to an exemplifying and non-limiting embodiment of the invention for manufacturing an instrument product.

FIG. 6 shows a flowchart of a method according to an exemplifying and non-limiting embodiment of the invention for manufacturing an instrument product that comprises a medical hand instrument and a radio frequency identifier readable from a distance away from the radio frequency identifier. The method comprises at least the following action:

action 601: placing the radio frequency identifier on a surface of the medical hand instrument and covering the radio frequency identifier at least partly with cover material so that the cover material gets attached with adhesive material to the surface of the medical hand instrument so that the adhesive material is in contact with both the cover material and the surface of the medical hand instrument, wherein the adhesive material is dispensed in fluidic form and allowed to cure.

In a method according to an exemplifying and non-limiting embodiment of the invention, the cover material is the same material as the adhesive material, and the covering is carried out by dispensing or casting the adhesive material in fluidic form to cover at least partly the radio frequency identifier attached with the adhesive material to the surface of the medical hand instrument.

A method according to an exemplifying and non-limiting embodiment of the invention comprises covering at least 90% of surface area the radio frequency identifier with the adhesive material.

A method according to an exemplifying and non-limiting embodiment of the invention comprises covering at least 95% of surface area the radio frequency identifier with the adhesive material.

A method according to an exemplifying and non-limiting embodiment of the invention comprises placing a mold element to surround the radio frequency identifier when the radio frequency identifier is on the surface of the medical hand instrument and injecting the adhesive material into the mold element. The method may further comprise removing the mold element from the instrument product. It is also possible that the mold element is not removed from the instrument product, i.e. the mold element is not only a tool used in the manufacture of the instrument product but also an element of the instrument product.

A method according to an exemplifying and non-limiting embodiment of the invention comprises placing the radio frequency identifier and the adhesive material into a mold element, and pressing the mold element containing the adhesive material and the radio frequency identifier against the surface of the medical hand instrument. The method may further comprise removing the mold element from the instrument product. It is also possible that the mold element is not removed from the instrument product.

In a method according to an exemplifying and non-limiting embodiment of the invention, the above-mentioned cover material constitutes a cover element comprising a cavity. In this exemplifying case, the method comprises inserting the radio frequency identifier in the cavity and then attaching the cover element to the surface of the medical hand instrument with the adhesive material so that the cavity opens towards the surface of the medical hand instrument. In a method according to an exemplifying and non-limiting embodiment of the invention, the cavity is dimensioned so that the cover element gets stretched when the radio frequency identifier is inserted in the cavity. In a method according to an exemplifying and non-limiting embodiment of the invention, an edge portion of the cavity is provided with at least one claw section for shape-locking the radio frequency identifier inside the cavity.

A method according to an exemplifying and non-limiting embodiment of the invention comprises positioning the radio frequency identifier so that the distance between the surface of the medical hand instrument and the radio frequency identifier is less than 1 mm, more advantageously less than 0.5 mm, yet more advantageously less than 0.2 mm, and yet more advantageously less than 0.05 mm.

In a method according to an exemplifying and non-limiting embodiment of the invention, the above-mentioned surface of the medical hand instrument is a surface of an elongated element of the medical hand instrument and the radio frequency identifier is placed substantially in the middle area of the elongated element of the medical hand instrument.

In a method according to an exemplifying and non-limiting embodiment of the invention, the radio frequency identifier has an elongated shape and the radio frequency identifier is attached to the medical hand instrument so that the longitudinal direction of the radio frequency identifier is substantially parallel with the longitudinal direction of the above-mentioned elongated element of the medical hand instrument.

A method according to an exemplifying and non-limiting embodiment of the invention comprises attaching the radio frequency identifier to an end-portion of an elongated element of the medical hand instrument so that the longitudinal directions of the elongated element of the medical hand instrument and the radio frequency identifier are substantially parallel with each other and an end-portion of the radio frequency identifier capable of emitting stronger radiation than the other end-portion of the radio frequency identifier points towards the middle area of the elongated element of the medical hand instrument.

The specific examples provided in the description given above should not be construed as limiting the scope and/or the applicability of the appended claims. Lists and groups of examples provided in the description given above are not exhaustive unless otherwise explicitly stated.

What is claimed is:

1. An instrument product comprising:
    a medical hand instrument, and
    a radio frequency identifier on a surface of the medical hand instrument, the radio frequency identifier being readable from a distance away from the radio frequency identifier,
wherein the radio frequency identifier is at least partly covered with cover material attached with adhesive material to the surface of the medical hand instrument so that the adhesive material is in contact with both the cover material and the surface of the medical hand instrument, the adhesive material being dispensable in fluidic form prior to curing, and wherein
    the radio frequency identifier has an elongated shape and an end-portion of the radio frequency identifier is capable of emitting stronger radiation than another end-portion of the radio frequency identifier,
    the surface of the medical hand instrument is a surface of an elongated element of the medical hand instrument, and
    the radio frequency identifier is located at an end-portion of the elongated element of the medical hand instrument so that i) longitudinal directions of the elongated element of the medical hand instrument and the radio frequency identifier are substantially parallel with each other and ii) the end-portion of the radio frequency identifier capable of emitting stronger radiation points towards a middle area of the medical hand instrument.

2. An instrument product according to claim 1, wherein at least 90% of surface area of the radio frequency identifier is covered by the adhesive material, wherein the cavity is dimensioned so that the cover element gets stretched in response to insertion of the radio frequency identifier in the cavity, wherein an edge portion of the cavity is provided with at least one claw section for shape-locking the radio frequency identifier inside the cavity, wherein a distance (d) between the surface of the medical hand instrument and the radio frequency identifier is less than 1 mm, wherein the radio frequency identifier is a ceramic radio frequency identifier tag, and wherein the surface of the medical hand instrument is a metal surface.

3. An instrument product comprising:
    a medical hand instrument, and
    a radio frequency identifier on a surface of the medical hand instrument, the radio frequency identifier being readable from a distance away from the radio frequency identifier,
wherein the radio frequency identifier is at least partly covered with cover material attached with adhesive material to the surface of the medical hand instrument so that the adhesive material is in contact with both the cover material and the surface of the medical hand instrument, the adhesive material being dispensable in fluidic form prior to curing, and wherein the surface of the medical hand instrument is a surface of an elongated element of the medical hand instrument, the radio frequency identifier has an elongated shape, the radio frequency identifier is located at an end-portion of the elongated element of the medical hand instrument so that longitudinal directions of the elongated element of the medical hand instrument and the radio frequency identifier are substantially parallel with each other and an end-portion of the radio frequency identifier capable of emitting stronger radiation than another end-portion of the radio frequency identifier points towards a middle area of the medical hand instrument.

4. An instrument product according to claim 3, wherein the cover material is same material as the adhesive material.

5. An instrument product according to claim 4, wherein at least 90% of surface area the radio frequency identifier is covered by the adhesive material.

6. An instrument product according to claim 4, wherein at least 95% of surface area the radio frequency identifier is covered by the adhesive material.

7. An instrument product according to claim 4, wherein a shape of a surface of a portion the adhesive material covering the radio frequency identifier is at least partly determined by a mold element.

8. An instrument product according to claim 7, wherein the instrument product comprises the mold element.

9. An instrument product according to claim 7, wherein the surface whose shape is at least partly determined by the mold element constitutes a part of an outer surface of the instrument product.

10. An instrument product according to claim 3, wherein the cavity is dimensioned so that the cover element gets stretched in response to insertion of the radio frequency identifier in the cavity.

11. An instrument product according to claim 3, wherein an edge portion of the cavity is provided with at least one claw section for shape-locking the radio frequency identifier inside the cavity.

12. An instrument product according to claim 3, wherein a distance (d) between the surface of the medical hand instrument and the radio frequency identifier is less than 1 mm.

13. An instrument product according to claim 3, wherein the radio frequency identifier is a ceramic radio frequency identifier tag.

14. An instrument product according to claim 3, wherein the surface of the medical hand instrument is a metal surface.

15. An instrument product according to claim 3, wherein the surface of the medical hand instrument is a surface of an elongated element of the medical hand instrument, and the radio frequency identifier is located substantially in a middle area of the elongated element of the medical hand instrument.

16. An instrument product according to claim 15, wherein the radio frequency identifier has an elongated shape and a longitudinal direction of the radio frequency identifier is substantially parallel with a longitudinal direction of the elongated element of the medical hand instrument.

17. A method for manufacturing an instrument product that comprises a medical hand instrument and a radio frequency identifier readable from a distance away from the radio frequency identifier, the method comprising placing the radio frequency identifier on a surface of the medical hand instrument, wherein the method comprises covering the radio frequency identifier at least partly with cover material so that the cover material gets attached with adhesive material to the surface of the medical hand instrument so that the adhesive material is in contact with both the cover material and the surface of the medical hand instrument, wherein the adhesive material is dispensed in fluidic form and allowed to cure and wherein the cover material is same material as the adhesive material, and the covering is carried out by dispensing or casting the adhesive material in fluidic form to cover at least partly the radio frequency identifier, and wherein the radio frequency identifier has an elongated shape and an end portion of the radio frequency identifier is capable of emitting stronger radiation than another end portion of the radio frequency identifier, the surface of the medical hand instrument is a surface of an elongated element of the medical hand instrument, and the radio frequency identifier is placed on an end portion of the elongated element of the medical hand instrument so that i) longitudinal directions of the elongated element of the medical hand instrument and the radio frequency identifier are substantially parallel with each other and ii) the end portion of the radio frequency identifier capable of emitting stronger radiation points towards a middle area of the medical hand instruments.

18. A method according to claim 17, wherein the method comprises placing a mold element to surround the radio frequency identifier when the radio frequency identifier is on the surface of the medical hand instrument, and injecting the adhesive material into the mold element or placing the radio frequency identifier and the adhesive material into a mold element, and pressing the mold element containing the adhesive material and the radio frequency identifier against the surface of the medical hand instrument.

19. A method according to claim 17, wherein the method comprises placing the radio frequency identifier and the adhesive material into a mold element, and pressing the mold element containing the adhesive material and the radio frequency identifier against the surface of the medical hand instrument.

20. A method according to claim 17, wherein the method comprises removing the mold element from the medical hand instrument.

\* \* \* \* \*